(12) United States Patent
Simon-Nobbe et al.

(10) Patent No.: US 7,247,441 B2
(45) Date of Patent: Jul. 24, 2007

(54) NUCLEIC ACID SEQUENCE AND PROTEIN IN ADDITION TO POLYPEPTIDES CODING FOR MANNITOL DEHYDROGENASES OR PARTS THEREOF AND THE PRODUCTION AND USE THEREOF IN DIAGNOSIS AND THERAPY

(75) Inventors: Birgit Simon-Nobbe, Salzburg (AT); Peter Schneider, Oberhofen (AT); Ursula Denk, Salzburg (AT); Verena Wally, Salzburg (AT); Klaus Richter, Salzburg (AT); Christian Radauer, Vienna (AT); Markus Teige, Vienna (AT); Christof Ebner, Brunn am Gebirge (AT); Michael Breitenbach, Salzburg (AT)

(73) Assignee: Biomay Produktions- Und Handels-Aktienge Sellschaft, Vienna (AT)

( * ) Notice: Subject to any disclaimer, the term of this patent is extended or adjusted under 35 U.S.C. 154(b) by 0 days.

(21) Appl. No.: 10/508,681

(22) PCT Filed: Mar. 19, 2003

(86) PCT No.: PCT/EP03/02873

§ 371 (c)(1),
(2), (4) Date: Jan. 24, 2005

(87) PCT Pub. No.: WO03/083098

PCT Pub. Date: Oct. 9, 2003

(65) Prior Publication Data

US 2005/0124055 A1    Jun. 9, 2005

(30) Foreign Application Priority Data

Mar. 28, 2002  (DE) ............................... 102 14 082
Jul. 24, 2002   (DE) ............................... 102 33 676

(51) Int. Cl.
*C12N 9/04*      (2006.01)
*C12N 1/20*      (2006.01)
*C12N 15/74*     (2006.01)
*C12P 21/06*     (2006.01)
*C07H 23/04*     (2006.01)
*A01N 63/00*     (2006.01)
*A61K 39/385*    (2006.01)

(52) U.S. Cl. ............... 435/7.1; 435/252.33; 435/254.1; 435/484; 435/69.1; 435/23.2; 435/190; 424/93.1; 424/94.1; 424/94.4; 424/171.1; 424/185.1; 424/194; 536/23.2

(58) Field of Classification Search ............. 424/184.1, 424/94.1, 94.4, 171.1, 185.1, 194, 93.1; 435/183, 435/68.1, 7.1, 252.33, 254.1, 484, 69.1, 23.2, 435/190; 530/300, 333; 536/23.2
See application file for complete search history.

(56) References Cited

OTHER PUBLICATIONS

Dreborg et al., A double-blind, muticenter immunotherapy trial in children, using a purified and standardized Caldosporium herbarum preparation. Allergy 41: 131-140, 1986.*
Horst et al., Double-blind, placebo-controlled rush immunotherapy with a standardized Alternaria extract. J. Allergy Clin. Immunol., 85(2): 460-472, 1990.*
Pike et al., Dec. 1, 2001, Database SWISSPROT, Accession No. Q96W29, XP-002244008, TrEMBL.*
Suvarna et al., Mannitol-1-phosphate dehydrogenase from Cryptococcus neoformans is a zinc-containing long chain alcohol/polyol dehydrogenase. Microbiology, 2000, vol. 146: 2705-2713.*
Noeldner et al., Purification and characterization of mannitol dehydrogenase from the fungal tomato pathogen Cladosporium fulvum. Mol. Plant Pathol., 1994, vol. 45: 281-289.*
Achatz et al., Molecular cloning of major and minor allergens of Alternaraia alternata and Cladosporium herbarum. Mol. Immunol., 1995, vol. 32 (3): 213-227.*
Pike M. et al., "Cladosporium Fulvum, NADP-dependent maqnnitol dehydrogenase", Database accession No. Q96W29, XP-002244008.
P. K-M. Noeldner et al., "Purification and characterization of mannitol dehydrogenase from the fungal tomato pathogen Cladosporium fulvum", Physiological and Molecular Plant Pathology, 1994, pp. 281-289, vol. 45.
Karl Hult et al., "The Distribution of the NADPH Regenerating Mannitol Cycle Among Fungal Species", Arch. Microbiol., 1980, pp. 253-255, vol. 128.
Vouge De M.W. et al., "Molecular Cloning of IgE-Binding Fragments of Alternaria alternata Allergens", Int Arch Allergy Immunol, 1998, pp. 261-268, vol. 116.
Michael Breitenbach et al., "Enolases Are Highly Conserved Fungal Allergens", Int Arch Allergy Immunol. 1997, pp. 114-117, vol. 113.

* cited by examiner

*Primary Examiner*—Rebecca E. Prouty
*Assistant Examiner*—Ganapathirama Raghu
(74) *Attorney, Agent, or Firm*—Heller Ehrman LLP

(57) ABSTRACT

The invention relates to polypeptides made of mannitol-dehydrogenase of *Cladosporium herbarum* and *Alternaria alternata* nucleic acids coding therefor and the use thereof in diagnosis and therapy.

3 Claims, 7 Drawing Sheets

```
CTG AAG GGC AAG GTC GTC GTC GTT ACC GGC GCT TCC GGC CCC
 L   K   G   K   V   V   V   V   T   G   A   S   G   P
AAG GGC ATG GGT ATT GAG GCC GCT CGC GGT TGC GCC GAG ATG
 K   G   M   G   I   E   A   A   R   G   C   A   E   M
GGC GCC GCT GTT GCC ATC ACC TAC GCC TCC CGC GCC CAG GGT
 G   A   A   V   A   I   T   Y   A   S   R   A   Q   G
GCT GAG GAG AAC GTC AAG GAG CTT GAG AAG ACC TAC GGC ATC
 A   E   E   N   V   K   E   L   E   K   T   Y   G   I
AAG GCC AAG GCC TAC AAG TGC CAG GTC GAC AGC TAC GAG TCC
 K   A   K   A   Y   K   C   Q   V   D   S   Y   E   S
TGC GAG AAG CTC GTC AAG GAC GTC GTT GCC GAC TTC GGC CAG
 C   E   K   L   V   K   D   V   V   A   D   F   G   Q
ATC GAT GCC TTC ATC GCC AAC GCC GGT GCC ACC GCC GAC TCT
 I   D   A   F   I   A   N   A   G   A   T   A   D   S
GGC ATC CTC GAC GGC TCC GTC GAG GCC TGG AAC CAC GTC GTC
 G   I   L   D   G   S   V   E   A   W   N   H   V   V
CAG GTC GAC CTG AAC GGT ACC TTC CAC TGC GCC AAG GCC GTT
 Q   V   D   L   N   G   T   F   H   C   A   K   A   V
CGC CAC CAC TTC AAG GAG CGT GGA ACC GGT TCC TTC GTC ATC
 G   H   H   F   K   E   R   G   T   G   S   F   V   I
ACC TCC TCC ATG TCC GGC CAC ATC GCC AAC TAT CCC CAG GAA
 T   S   S   M   S   G   H   I   A   N   Y   P   Q   E
CAG ACC TCC TAC AAC GTC GCC AAG GCT GGA TGC ATC CAC ATG
 Q   T   S   Y   N   V   A   K   A   G   C   I   H   M
GCT CGC TCC TTG GCA
 A   R   S   L   A
```

Alignment of the C. fulvum and C. herbarum NADP-MtDHs on the basis of the available DNA and protein data

```
C.fulvum     1  MPQRIPEAEHLLDLLSLKGVVVVTGASGPKGMGIEAARGCAEMGADGAITYASPAEGL
C.herbarum      PGQQATKHESDLDCLSLKGVVVVTGASGPKGMGIEAARGCAEMGAHGAITYASRACGE C.fulvum    61  KNAEELSRQYGIKCKAYKCQVDKYESVECLVKDVEQDFGKIDAFIANAGATAESGILDGS
C.herbarum      ENVKELEKTYGIKAKAYKCCVDSYESCQKLVKDVTADFGCIDAFIANAGATADSGILDGS C.fulvum   121  VEDWNHVVQVDLNGTFHCAKAVGHHFKERGTGSFVITSSMSGHIANYPQEQTSYNVAKAG
C.herbarum      VEFWNHVVQVDLNGTFHCAKAVGHHFKERGTGSFVITSSMSGHIANYPQEQTSYNVAKAG C.fulvum   181  CIHMARSLAHEWRDFARVTSISPGYEDTGLSDFVAKDIQKLVHSMIPLGRDGLAKELKGA
C.herbarum      CIHMARSLA--------------DTGLSDFVK-----------GRDGLAKEL---

C.fulvum   241  YVYLVSDASTYTTGADIVIDGGYTCR
C.herbarum      --------------------------
```

Alignment of the derived amino acid sequences of the Cladosporium herbarum and Cladosporium fulvum mannitol dehydrogenases.

- ... means that the amino acid sequence of C. herbarum still requires sequencing at this position.

Fig. 3: Complete nucleotide and protein sequence of the Cladosporium herbarum MtDH

```
CCGTCTACACACGCAACTTCCCGCCTCGACTCCATATCCAATCACATCAAG                    51
ATG CCT GGC CAG CAA GCA ACC AAG CAT GAG TCC CTT TTG GAC CAG CTC        99
 M   P   G   Q   Q   A   T   K   H   E   S   L   L   D   Q   L         16

TCC CTG AAG GGC AAG GTC GTC GTC GTC ACC GGC GCT TCC GGC CCC AAG        147
 S   L   K   G   K   V   V   V   V   T   G   A   S   G   P   K         32

GGC ATG GGT ATT GAG GCC GCT CGC GGT TGC GCC GAG ATG GGC GCC GCT        195
 G   M   G   I   E   A   A   R   G   C   A   E   M   G   A   A         48

GTT GCC ATC ACC TAC GCC TCC CGC GCC CAG GGT GCT GAG GAG AAC GTC        243
 V   A   I   T   Y   A   S   R   A   Q   G   A   E   E   N   V         64

AAG GAG CTT GAG AAG ACC TAC GGC ATC AAG GCC AAG GCC TAC AAG TGC        291
 K   E   L   E   K   T   Y   G   I   K   A   K   A   Y   K   C         80

CAG GTC GAC AGC TAC GAG TCC TGC GAG AAG CTC GTC AAG GAC GTC GTT        339
 Q   V   D   S   Y   E   S   C   E   K   L   V   K   D   V   V         96

GCC GAC TTC GGC CAG ATC GAT GCC TTC ATC GCC AAC GCC GGT GCC ACC        387
 A   D   F   G   Q   I   D   A   F   I   A   N   A   G   A   T         112

GCC GAC TCT GGC ATC CTC GAC GGC TCC GTC GAG GCC TGG AAC CAC GTC        435
 A   D   S   G   I   L   D   G   S   V   E   A   W   N   H   V         128

GTC CAG GTC GAC CTG AAC GGT ACC TTC CAC TGC GCC AAG GCC GTT GGC        483
 V   Q   V   D   L   N   G   T   F   H   C   A   K   A   V   G         144

CAC CAC TTC AAG GAG CGT GGA ACC GGT TCC CTC GTC ATC ACC GCC TCC        531
 H   H   F   K   E   R   G   T   G   S   L   V   I   T   A   S         160

ATG TCC GGC CAC ATC GCC AAC TTC CCC CAG GAG CAG ACC TCC TAC AAC        579
 M   S   G   H   I   A   N   F   P   Q   E   Q   T   S   Y   N         176

GTC GCC AAG GCT GGC TGC ATC CAC ATG GCT CGC TCC CTC GCC AAC GAG        627
 V   A   K   A   G   C   I   H   M   A   R   S   L   A   N   E         192

TGG CGC GAC TTC GCC CGT GTC AAC TCC ATC TCC CCC GGT TAC ATT GAC        675
 W   R   D   F   A   R   V   N   S   I   S   P   G   Y   I   D         208

ACT GGT CTC TCC GAC TTC GTT CCC AAG GAG ACC CAG CAG CTC TGG CAC        723
 T   G   L   S   D   F   V   P   K   E   T   Q   Q   L   W   H         224

TCC ATG ATC CCC ATG GGC CGT GAC GGT CTC GCC AAG GAG CTC AAG GGC        771
 S   M   I   P   M   G   R   D   G   L   A   K   E   L   K   G         240

GCC TAC GTC TAC TTC GCC TCC GAC GCC TCC ACC TAC ACC ACC GGT GCC        819
 A   Y   V   Y   F   A   S   D   A   S   T   Y   T   T   G   A         256

GAT CTC CTC ATT GAC GGT GGT TAC ACC ACC AGA TAA                        855
 D   L   L   I   D   G   G   Y   T   T   R   *                         268
GCGACTCGCCCACAGCAAGTCGTTGAGGCGGAAGGACAAAAAAAAAAAAAAAAAAAAAAAAA         918
```

```
Met Pro Ile Thr Val Pro Gln Ala Thr Glu Leu Lys Asp Leu Phe Ser
 1           5               10                  15
Leu Lys Gly Lys Val Val Ile Val Thr Gly Ala Ser Gly Pro Thr Gly
            20                  25                  30
Ile Gly Thr Glu Ala Ala Arg Gly Cys Ala Glu Tyr Gly Ala Asp Leu
        35              40                  45
Ala Ile Thr Tyr Asn Ser Arg Ala Glu Gly Ala Glu Lys Asn Ala Lys
        50              55                  60
Glu Met Ser Glu Lys Tyr Gly Val Lys Val Lys Ala Tyr Lys Cys Gln
 65              70                  75                      80
Val Asn Glu Tyr Ala Gln Cys Glu Lys Leu Val Gln Asp Val Ile Lys
                85                  90                  95
Asp Phe Gly Lys Val Asp Val Phe Ile Ala Asn Ala Gly Lys Thr Ala
               100             105                 110
Asp Asn Gly Ile Leu Asp Ala Thr Val Glu Gln Trp Asn Glu Val Ile
            115                 120                 125
Gln Thr Asp Leu Thr Gly Thr Phe Asn Cys Ala Arg Ala Val Gly Leu
    130                 135                 140
His Phe Arg Glu Arg Lys Thr Gly Ser Leu Val Ile Thr Ser Ser Met
145                 150                 155                 160
Ser Gly His Ile Ala Asn Phe Pro Gln Glu Gln Ala Ser Tyr Asn Val
            165                 170                 175
Ala Lys Ala Gly Cys Ile His Leu Ala Lys Ser Leu Ala Asn Glu Trp
            180                 185                 190
Arg Asp Phe Ala Arg Val Asn Ser Ile Ser Pro Gly Tyr Ile Asp Thr
        195                 200                 205
Gly Leu Ser Asp Phe Val Pro Gln Asp Ile Gln Lys Leu Trp His Ser
    210                 215                 220
Met Ile Pro Met Gly Arg Asp Ala Lys Ala Thr Glu Leu Lys Gly Ala
225             230                 235                 240
Tyr Val Tyr Phe Ala Ser Asp Ala Ser Ser Tyr Cys Thr Gly Ser Asp
                245                 250                 255
Leu Leu Ile Asp Gly Gly Tyr Cys Val Arg
            260             265
```

Fig. 4: Alternaria alternata MtDH (Seq. ID No. 11)

Alternaria alternata MtDH

```
CTTCATATCACATCACACTTCAA                                                 23
CTCAATTCCCATTTTATATACCCCAAACTTCTTTACTCTTCATAAACCCACATAATCGCCACA         86
ATG CCC ATC ACC GTT CCC CAA GCT ACC GAG CTC AAG GAC CTC TTC AGC        134
 M   P   I   T   V   P   Q   A   T   E   L   K   D   L   F   S         16
CTT AAG GGC AAG GTC GTC ATC GTC ACC GGT GCC TCC GGC CCC ACC GGT        182
 L   K   G   K   V   V   I   V   T   G   A   S   G   P   T   G         32
ATT GGC ACA GAG GCT GCC CGA GGA TGC GCT GAG TAC GGT GCC GAC CTC        230
 I   G   T   E   A   A   R   G   C   A   E   Y   G   A   D   L         48
GCC ATC ACC TAC AAC TCT CGC GCC GAG GGT GCC GAG AAG AAC GCA AAG        278
 A   I   T   Y   N   S   R   A   E   G   A   E   K   N   A   K         64
GAG ATG AGC GAG AAG TAC GGC GTC AAG GTC AAG GCC TAC AAG TGC CAG        326
 E   M   S   E   K   Y   G   V   K   V   K   A   Y   K   C   Q         80
GTC AAC GAG TAC GCT CAG TGC GAG AAG CTC GTC CAG GAC GTC ATC AAG        374
 V   N   E   Y   A   Q   C   E   K   L   V   Q   D   V   I   K         96
GAC TTC GGC AAG GTC GAT GTC TTC ATC GCC AAC GCC GGA AAG ACT GCC        422
 D   F   G   K   V   D   V   F   I   A   N   A   G   K   T   A        112
GAC AAC GGT ATC CTC GAC GCT ACC GTT GAG CAG TGG AAC GAG GTC ATC        470
 D   N   G   I   L   D   A   T   V   E   Q   W   N   E   V   I        128
CAG ACC GAC TTG ACC GGT ACC TTC AAC TGC GCC CGT GCC GTT GGT CTC        518
 Q   T   D   L   T   G   T   F   N   C   A   R   A   V   G   L        144
CAC TTC CGC GAG CGC AAG ACT GGC TCT CTC GTC ATC ACC TCC TCC ATG        566
 H   F   R   E   R   K   T   G   S   L   V   I   T   S   S   M        160
TCC GGC CAC ATT GCC AAC TTC CCC CAG GAG CAG GCC TCC TAC AAC GTT        614
 S   G   H   I   A   N   F   P   Q   E   Q   A   S   Y   N   V        176
GCT AAG GCT GGC TGC ATT CAC CTC GCC AAG TCG CTC GCC AAC GAG TGG        662
 A   K   A   G   C   I   H   L   A   K   S   L   A   N   E   W        192
AGG GAC TTT GCC CGT GTC AAC TCC ATC TCC CCT GGA TAC ATT GAC ACT        710
 R   D   F   A   R   V   N   S   I   S   P   G   Y   I   D   T        208
GGT CTC TCC GAC TTC GTT CCC CAG GAC ATC CAG AAG CTG TGG CAC TCC        758
 G   L   S   D   F   V   P   Q   D   I   Q   K   L   W   H   S        224
ATG ATC CCC ATG GGC CGT GAC GCC AAG GCT ACT GAG CTC AAG GGT GCC        806
 M   I   P   M   G   R   D   A   K   A   T   E   L   K   G   A        240
TAC GTC TAC TTC GCA TCG GAT GCC TCA TCC TAC TGC ACT GGT TCC GAT        854
 Y   V   Y   F   A   S   D   A   S   S   Y   C   T   G   S   D        256
CTC CTC ATC GAC GGT GGT TAC TGC GTC AGG TAA                            887
 L   L   I   D   G   G   Y   C   V   R   *                            267
ACGTGTCATTCCGGAAGGAAGATGCGAGTGGAGGAATATAATAATGGACGACGTCTTGCCGGA         950
AGTCTTGTGTCCATGTAAATAGCATCGAGACATCAATAAAGCTTCGCAGGTTTCACATCACAA        1013
AAAAAAAAAAAAA                                                         1026
```

Fig. 5: DNA sequence (seq. ID No. 12) of the Alternaria alternata mannitol dehydrog

```
C.herbarum    1   ATGCCTGGCCAGCAAGCAACGAAGCATGAGTCCCTTTTGGACCAGCTCTCCCTGAAGGGC
A.alternata   1   ATGCCC---ATCACCGTTCCCCAAGCTACCGAGCTCAAGGACCTCTTCAGCCTTAAGGGC C.herbarum    61  AAGGTCGTCGTCGTCACCGGCGGTTCCGGCCCAAGGGCATGGTATTGAGGCCGGTCGC
A.alternata   58  AAGGTCGTCATCGTCACCGGTGCCTCCGGCCCCACCGGTATTGGCACAGAGGCTGCCGA C.herbarum    121 GGTTGCGCCGAGATGGGCGCCGCTGTTGCCATCACCTACGCCTCCCGCGCCCAGGGTGCT
A.alternata   118 GCATGCGCTGAGTACGGTTCCCGACCTCGCCATCACCTACAACTCTCGCGCCCAGGGTGCC C.herbarum    181 GAGGAGAACGTCAAGGAGCTTGAGAAGACCTACGGCATCAAGGCCAACGCCTACAAGTGC
A.alternata   178 GAGAAGAACGCAAAGGAGATCGAGCGAGAAGTACGGCGTCAAGGTCAAGGCCTACAAGTGC C.herbarum    241 CAGGTCGACAGCTACGAGTCCTGCGAGAAGCTCGTCAAGGACGTCGTTGCCGACTTCGGC
A.alternata   238 CAGGTCAACGAGTACGCTCAGTGCGAGAAGCTCGTCCAGGACGTCATCAAGGACTTCGGC C.herbarum    301 CAGATCGATGCCTTCATCGCCAACGCCGGTGCCACCGCCGACTCTGGCATCCTCGACGGC
A.alternata   298 AAGGTCGATGTCTTCATCGCCAACGCCGGAAAGACTGCCGACAACGGTATCCTCGACGCT C.herbarum    361 TCCGTCGAGGCCTGGAACCACGTCGTCCAGGTCGACCTGAACGGTACCTTCCACTGCGCC
A.alternata   358 ACCGTTGAGCAGTGGAACGAGGTCATCCAGACCGACTTGACCGGTACCTTCAACTGCGCC C.herbarum    421 ATGGCCGTTGGCCACCACTTCAAGGAGCGTGGAACCGGTTCCCTCGTCATCACCGCCTCC
A.alternata   418 CTGCCCGTTGGTGTTCCACTTCCGCGAGCGCAAGACTGGCTCTCTCGTCATCACCTCCTCC C.herbarum    481 ATGTCCGGCCACATCGCCAACTTCCCCCAGGAGCAGACCTCCTACAACGTCGCCAAGGCT
A.alternata   478 ATGTCCGGCCACATTGCCAACTTCCCCCAGGAGCAGGCCTCCTACAACGTTGCTAAGGCT C.herbarum    541 GGCTGCATCCACATGGCTCGCTCCCTCGCCAACGAGTGGCGCGACTTCGCCCGTGTCAAC
A.alternata   538 GGCTGCATTCACCTCGCCAAGTCGCTCGCCAACGAGTGGAGGGACTTTGCCCGTGTCAAC C.herbarum    601 TCCATCTCCCCCGGTTACATTGACACTGGTCTCTCCGACTTCGTTCCCAAGGACACCCAG
A.alternata   598 TCCATCTCCCCCTGGATACATTGACACTGGTCTCTCCGACTTCGTTCCCAGGACATCCAG C.herbarum    661 CAGCTCTGGCACTCCATGATCCCCATGGGCCGTGACGGTCTCGCCAAGGAGCTCAAGGGC
A.alternata   658 AAGCTGTGGCACTCCATGATCCCCATGGGCCGTGACGCCAAGGCTACTGAGCTCAAGGCT C.herbarum    721 GCCTACGTCTACTTCGCCTCCGACGCCTCCACCTACACCACCGGTGCCGATCTCCTCATT
A.alternata   718 GCCTACGTCTACTTCGCATCGGATGCCTCATCCTACTGCAGTGGTTCCGATCTCCTCATC
```

Fig. 6: Alignment of the C. herbarum and A. alternata DNA sequences

```
C.herbarum    781 GACGGTGGTTACACGACCAGATAA
A.alternata   778 GACGGTGGTTACTCAGTACGCAA C.herbarum      1 MBGQQATKHESILPQLSLKGAKVYTCASCDCHSTCAAMQLARMGAVAITBAGWAQRA
A.alternata     1 MH-ITVPQATEDKSLTSLSGRVVTTGASCITCSAAPCCATGRDLAITYSRALSA C.herbarum     61 REVKLIEKTVGIPAHATECCDSNESCFHLMOGVAKCQHAEKANAGAPADSHILDC
A.alternata    60 EKNAKERSEKMGUEVEAPECCWMZDACQERKAQDVIKDHLAVQVETAINGKTADNSILUA C.herbarum    121 SVLARAGEVMVQINSTGMPAKAKCBHGKARCTGCLVITAGHSCHIAHIPOKLASTHVAKA
A.alternata   120 AVEQRGENIGTDLVSTDNIARAVCLHPFPEIAGSLVIPASHSGHIAHMPOLDASYHVAKA C.herbarum    181 GCTHMARSLAHEARDFAPVMSLSPGYIDTSLSDFVKRTROAUELTHMGREGLAKELRG
A.alternata   180 GCIHLAKSLANEURDPAKVESISTHYIDTHLSDFVSQTIPLSHSHIPMGHGRGATSLRG C.herbarum    241 AYVYFASQASTVTFGADLLIDGGHTVE
A.alternata   240 AYVYFASQASSYCTGSDLLIDGGRCVP
```

FIG. 7

SEQUENCE LISTING

<160> NUMBER OF SEQ ID NOS: 12

<210> SEQ ID NO 1
<211> LENGTH: 173
<212> TYPE: PRT
<213> ORGANISM: Cladosporium herbarum

<400> SEQUENCE: 1

```
Leu Lys Gly Lys Val Val Val Thr Gly Ala Ser Gly Pro Lys Gly
 1               5                  10                  15

Met Gly Ile Glu Ala Ala Arg Gly Cys Ala Glu Met Gly Ala Ala Val
                20                  25                  30

Ala Ile Thr Tyr Ala Ser Arg Ala Gln Gly Ala Glu Glu Asn Val Lys
            35                  40                  45

Glu Leu Glu Lys Thr Tyr Gly Ile Lys Ala Lys Ala Tyr Lys Cys Gln
        50                  55                  60

Val Asp Ser Tyr Glu Ser Cys Glu Lys Leu Val Lys Asp Val Val Ala
    65                  70                  75                  80

Asp Phe Gly Gln Ile Asp Ala Phe Ile Ala Asn Ala Gly Ala Thr Ala
                85                  90                  95

Asp Ser Gly Ile Leu Asp Gly Ser Val Glu Ala Trp Asn His Val Val
                100                 105                 110

Gln Val Asp Leu Asn Gly Thr Phe His Cys Ala Lys Ala Val Gly His
            115                 120                 125

His Phe Lys Glu Arg Gly Thr Gly Ser Phe Val Ile Thr Ser Ser Met
    130                 135                 140

Ser Gly His Ile Ala Asn Tyr Pro Gln Glu Gln Thr Ser Tyr Asn Val
145                 150                 155                 160

Ala Lys Ala Gly Cys Ile His Met Ala Arg Ser Leu Ala
                165                 170
```

<210> SEQ ID NO 2
<211> LENGTH: 519
<212> TYPE: DNA
<213> ORGANISM: Cladosporium herbarum

<400> SEQUENCE: 2

```
ctgaagggca aggtcgtcgt cgttaccggc gcttccggcc ccaagggcat gggtattgag    60
gccgctcgcg gttgcgccga gatgggcgcc gctgttgcca tcacctacgc ctcccgcgcc   120
cagggtgctg aggagaacgt caaggagctt gagaagacct acggcatcaa ggccaaggcc   180
tacaagtgcc aggtcgacag ctacgagtcc tgcgagaagc tcgtcaagga cgtcgttgcc   240
gacttcggcc agatcgatgc cttcatcgcc aacgccggtg ccaccgccga ctctggcatc   300
ctcgacggct ccgtcgaggc ctggaaccac gtcgtccagg tcgacctgaa cggtaccttc   360
```

```
cactgcgcca aggccgttgg ccaccacttc aaggagcgtg gaaccggttc cttcgtcatc    420
acctcctcca tgtccggcca catcgccaac tatccccagg aacagacctc ctacaacgtc    480
gccaaggctg gatgcatcca catggctcgc tccttggca                          519
```

<210> SEQ ID NO 3
<211> LENGTH: 266
<212> TYPE: PRT
<213> ORGANISM: Cladosporium fulvum

<400> SEQUENCE: 3

```
Met Pro Gln Arg Ile Pro Glu Ala Glu His Leu Leu Asp Leu Leu Ser
  1               5                  10                  15

Leu Lys Gly Arg Val Val Val Thr Gly Ala Ser Gly Pro Lys Gly
             20                  25                  30

Met Gly Ile Glu Ala Ala Arg Gly Cys Ala Glu Met Gly Ala Asp Leu
         35                  40                  45

Ala Ile Thr Tyr Ala Ser Arg Ala Glu Gly Gly Leu Lys Asn Ala Glu
     50                  55                  60

Glu Leu Ser Lys Gln Tyr Gly Ile Lys Cys Lys Ala Tyr Lys Cys Gln
 65                  70                  75                  80

Val Asp Lys Tyr Glu Ser Val Glu Gln Leu Val Lys Asp Val Ile Gln
                 85                  90                  95

Asp Phe Gly Lys Ile Asp Ala Phe Ile Ala Asn Ala Gly Ala Thr Ala
            100                 105                 110

Asn Ser Gly Ile Leu Asp Gly Ser Val Glu Asp Trp Asn His Val Val
        115                 120                 125

Gln Val Asp Leu Asn Gly Thr Phe His Cys Ala Lys Ala Val Gly His
    130                 135                 140

His Phe Lys Glu Arg Gly Thr Gly Ser Phe Val Ile Thr Ser Ser Met
145                 150                 155                 160

Ser Gly His Ile Ala Asn Tyr Pro Gln Glu Gln Thr Ser Tyr Asn Val
                165                 170                 175

Ala Lys Ala Gly Cys Ile His Met Ala Arg Ser Leu Ala Asn Glu Trp
            180                 185                 190

Arg Asp Phe Ala Arg Val Asn Ser Ile Ser Pro Gly Tyr Ile Asp Thr
        195                 200                 205

Gly Leu Ser Asp Phe Val Ala Lys Asp Ile Gln Lys Leu Trp His Ser
    210                 215                 220

Met Ile Pro Leu Gly Arg Asp Gly Leu Ala Lys Glu Leu Lys Gly Ala
225                 230                 235                 240

Tyr Val Tyr Leu Val Ser Asp Ala Ser Thr Tyr Thr Thr Gly Ala Asp
                245                 250                 255

Ile Val Ile Asp Gly Gly Tyr Thr Cys Arg
            260                 265
```

<210> SEQ ID NO 4
<211> LENGTH: 16
<212> TYPE: PRT
<213> ORGANISM: Cladosporium herbarum

<400> SEQUENCE: 4

```
Pro Gly Gln Gln Ala Thr Lys His Glu Ser Leu Leu Asp Gln Leu Ser
  1               5                  10                  15
```

<210> SEQ ID NO 5

<211> LENGTH: 11
<212> TYPE: PRT
<213> ORGANISM: Cladosporium herbarum

<400> SEQUENCE: 5

Leu Asp Thr Gly Leu Ser Asp Phe Val Val Lys
 1               5                  10

<210> SEQ ID NO 6
<211> LENGTH: 10
<212> TYPE: PRT
<213> ORGANISM: Cladosporium herbarum

<400> SEQUENCE: 6

Met Gly Arg Asp Gly Leu Ala Lys Glu Leu
 1               5                  10

<210> SEQ ID NO 7
<211> LENGTH: 918
<212> TYPE: DNA
<213> ORGANISM: Cladosporium herbarum

<400> SEQUENCE: 7

```
ccgtctacac acgcaacttc ccgcctcgac tccatatcca atcacatcaa gatgcctggc        60
cagcaagcaa ccaagcatga gtcccttttg gaccagctct ccctgaaggg caaggtcgtc       120
gtcgtcaccg gcgcttccgg ccccaagggc atgggtattg aggccgctcg cggttgcgcc       180
gagatgggcg ccgctgttgc catcacctac gcctcccgcg cccagggtgc tgaggagaac       240
gtcaaggagc ttgagaagac ctacggcatc aaggccaagg cctacaagtg ccaggtcgac       300
agctacgagt cctgcgagaa gctcgtcaag gacgtcgttg ccgacttcgg ccagatcgat       360
gccttcatcg ccaacgccgg tgccaccgcc gactctggca tcctcgacgg ctccgtcgag       420
gcctggaacc acgtcgtcca ggtcgacctg aacggtacct tccactgcgc caaggccgtt       480
ggccaccact tcaaggagcg tggaaccggt tccctcgtca tcaccgcctc catgtccggc       540
cacatcgcca acttcccccca ggagcagacc tcctacaacg tcgccaaggc tggctgcatc       600
cacatggctc gctccctcgc caacgagtgg cgcgacttcg cccgtgtcaa ctccatctcc       660
cccggttaca ttgacactgg tctctccgac ttcgttccca aggagaccca gcagctctgg       720
cactccatga tccccatggg ccgtgacggt ctcgccaagg agctcaaggg cgcctacgtc       780
tacttcgcct ccgacgcctc cacctacacc accggtgccg atctcctcat tgacggtggt       840
tacaccacca gataagcgac tcgcccacag caagtcgttg aggcggaagg acaaaaaaaa       900
aaaaaaaaaa aaaaaaaa                                                    918
```

<210> SEQ ID NO 8
<211> LENGTH: 267
<212> TYPE: PRT
<213> ORGANISM: Cladosporium herbarum

<400> SEQUENCE: 8

Met Pro Gly Gln Gln Ala Thr Lys His Glu Ser Leu Leu Asp Gln Leu
 1               5                  10                  15

Ser Leu Lys Gly Lys Val Val Val Thr Gly Ala Ser Gly Pro Lys
             20                  25                  30

Gly Met Gly Ile Glu Ala Ala Arg Gly Cys Ala Glu Met Gly Ala Ala
         35                  40                  45

Val Ala Ile Thr Tyr Ala Ser Arg Ala Gln Gly Ala Glu Glu Asn Val
     50                  55                  60

-continued

Lys Glu Leu Glu Lys Thr Tyr Gly Ile Lys Ala Lys Ala Tyr Lys Cys
 65                  70                  75                  80

Gln Val Asp Ser Tyr Glu Ser Cys Glu Lys Leu Val Lys Asp Val Val
                 85                  90                  95

Ala Asp Phe Gly Gln Ile Asp Ala Phe Ile Ala Asn Ala Gly Ala Thr
            100                 105                 110

Ala Asp Ser Gly Ile Leu Asp Gly Ser Val Glu Ala Trp Asn His Val
            115                 120                 125

Val Gln Val Asp Leu Asn Gly Thr Phe His Cys Ala Lys Ala Val Gly
130                 135                 140

His His Phe Lys Glu Arg Gly Thr Gly Ser Leu Val Ile Thr Ala Ser
145                 150                 155                 160

Met Ser Gly His Ile Ala Asn Phe Pro Gln Glu Gln Thr Ser Tyr Asn
                165                 170                 175

Val Ala Lys Ala Gly Cys Ile His Met Ala Arg Ser Leu Ala Asn Glu
            180                 185                 190

Trp Arg Asp Phe Ala Arg Val Asn Ser Ile Ser Pro Gly Tyr Ile Asp
            195                 200                 205

Thr Gly Leu Ser Asp Phe Val Pro Lys Glu Thr Gln Gln Leu Trp His
        210                 215                 220

Ser Met Ile Pro Met Gly Arg Asp Gly Leu Ala Lys Glu Leu Lys Gly
225                 230                 235                 240

Ala Tyr Val Tyr Phe Ala Ser Asp Ala Ser Thr Tyr Thr Thr Gly Ala
                245                 250                 255

Asp Leu Leu Ile Asp Gly Gly Tyr Thr Thr Arg
            260                 265

<210> SEQ ID NO 9
<211> LENGTH: 266
<212> TYPE: PRT
<213> ORGANISM: Cladosporium fulvum

<400> SEQUENCE: 9

Met Pro Gln Arg Ile Pro Glu Ala Glu His Leu Leu Asp Leu Leu Ser
 1               5                  10                  15

Leu Lys Gly Arg Val Val Val Thr Gly Ala Ser Gly Pro Lys Gly
            20                  25                  30

Met Gly Ile Glu Ala Ala Arg Gly Cys Ala Glu Met Gly Ala Asp Leu
            35                  40                  45

Ala Ile Thr Tyr Ala Ser Arg Ala Glu Gly Gly Leu Lys Asn Ala Glu
     50                  55                  60

Glu Leu Ser Lys Gln Tyr Gly Ile Lys Cys Lys Ala Tyr Lys Cys Gln
 65                  70                  75                  80

Val Asp Lys Tyr Glu Ser Val Glu Gln Leu Val Lys Asp Val Ile Gln
                 85                  90                  95

Asp Phe Gly Lys Ile Asp Ala Phe Ile Ala Asn Ala Gly Ala Thr Ala
            100                 105                 110

Asn Ser Gly Ile Leu Asp Gly Ser Val Glu Asp Trp Asn His Val Val
            115                 120                 125

Gln Val Asp Leu Asn Gly Thr Phe His Cys Ala Lys Ala Val Gly His
130                 135                 140

His Phe Lys Glu Arg Gly Thr Gly Ser Phe Val Ile Thr Ser Ser Met
145                 150                 155                 160

Ser Gly His Ile Ala Asn Tyr Pro Gln Glu Gln Thr Ser Tyr Asn Val

```
                    165                 170                 175
Ala Lys Ala Gly Cys Ile His Met Ala Arg Ser Leu Ala Asn Glu Trp
            180                 185                 190

Arg Asp Phe Ala Arg Val Asn Ser Ile Ser Pro Gly Tyr Ile Asp Thr
        195                 200                 205

Gly Leu Ser Asp Phe Val Ala Lys Asp Ile Gln Lys Leu Trp His Ser
    210                 215                 220

Met Ile Pro Leu Gly Arg Asp Gly Leu Ala Lys Glu Leu Lys Gly Ala
225                 230                 235                 240

Tyr Val Tyr Leu Val Ser Asp Ala Ser Thr Tyr Thr Thr Gly Ala Asp
            245                 250                 255

Ile Val Ile Asp Gly Gly Tyr Thr Cys Arg
            260                 265

<210> SEQ ID NO 10
<211> LENGTH: 267
<212> TYPE: PRT
<213> ORGANISM: Cladosporium herbarum

<400> SEQUENCE: 10

Met Pro Gly Gln Gln Ala Thr Lys His Glu Ser Leu Leu Asp Gln Leu
 1               5                  10                  15

Ser Leu Lys Gly Lys Val Val Val Thr Gly Ala Ser Gly Pro Lys
            20                  25                  30

Gly Met Gly Ile Glu Ala Ala Arg Gly Cys Ala Glu Met Gly Ala Ala
        35                  40                  45

Val Ala Ile Thr Tyr Ala Ser Arg Ala Gln Gly Ala Glu Glu Asn Val
    50                  55                  60

Lys Glu Leu Glu Lys Thr Tyr Gly Ile Lys Ala Lys Ala Tyr Lys Cys
65                  70                  75                  80

Gln Val Asp Ser Tyr Glu Ser Cys Glu Lys Leu Val Lys Asp Val Val
            85                  90                  95

Ala Asp Phe Gly Gln Ile Asp Ala Phe Ile Ala Asn Ala Gly Ala Thr
            100                 105                 110

Ala Asp Ser Gly Ile Leu Asp Gly Ser Val Glu Ala Trp Asn His Val
        115                 120                 125

Val Gln Val Asp Leu Asn Gly Thr Phe His Cys Ala Lys Ala Val Gly
    130                 135                 140

His His Phe Lys Glu Arg Gly Thr Gly Ser Leu Val Ile Thr Ala Ser
145                 150                 155                 160

Met Ser Gly His Ile Ala Asn Phe Pro Gln Glu Gln Thr Ser Tyr Asn
            165                 170                 175

Val Ala Lys Ala Gly Cys Ile His Met Ala Arg Ser Leu Ala Asn Glu
            180                 185                 190

Trp Arg Asp Phe Ala Arg Val Asn Ser Ile Ser Pro Gly Tyr Ile Asp
        195                 200                 205

Thr Gly Leu Ser Asp Phe Val Pro Lys Glu Thr Gln Gln Leu Trp His
    210                 215                 220

Ser Met Ile Pro Met Gly Arg Asp Gly Leu Ala Lys Glu Leu Lys Gly
225                 230                 235                 240

Ala Tyr Val Tyr Phe Ala Ser Asp Ala Ser Thr Tyr Thr Thr Gly Ala
            245                 250                 255

Asp Leu Leu Ile Asp Gly Gly Tyr Thr Thr Arg
            260                 265
```

<210> SEQ ID NO 11
<211> LENGTH: 266
<212> TYPE: PRT
<213> ORGANISM: Alternaria alternata

<400> SEQUENCE: 11

```
Met Pro Ile Thr Val Pro Gln Ala Thr Glu Leu Lys Asp Leu Phe Ser
 1               5                  10                  15
Leu Lys Gly Lys Val Val Ile Val Thr Gly Ala Ser Gly Pro Thr Gly
                20                  25                  30
Ile Gly Thr Glu Ala Ala Arg Gly Cys Ala Glu Tyr Gly Ala Asp Leu
            35                  40                  45
Ala Ile Thr Tyr Asn Ser Arg Ala Glu Gly Ala Glu Lys Asn Ala Lys
        50                  55                  60
Glu Met Ser Glu Lys Tyr Gly Val Lys Val Lys Ala Tyr Lys Cys Gln
 65                  70                  75                  80
Val Asn Glu Tyr Ala Gln Cys Glu Lys Leu Val Gln Asp Val Ile Lys
                85                  90                  95
Asp Phe Gly Lys Val Asp Val Phe Ile Ala Asn Ala Gly Lys Thr Ala
            100                 105                 110
Asp Asn Gly Ile Leu Asp Ala Thr Val Glu Gln Trp Asn Glu Val Ile
        115                 120                 125
Gln Thr Asp Leu Thr Gly Thr Phe Asn Cys Ala Arg Ala Val Gly Leu
130                 135                 140
His Phe Arg Glu Arg Lys Thr Gly Ser Leu Val Ile Thr Ser Ser Met
145                 150                 155                 160
Ser Gly His Ile Ala Asn Phe Pro Gln Glu Gln Ala Ser Tyr Asn Val
                165                 170                 175
Ala Lys Ala Gly Cys Ile His Leu Ala Lys Ser Leu Ala Asn Glu Trp
            180                 185                 190
Arg Asp Phe Ala Arg Val Asn Ser Ile Ser Pro Gly Tyr Ile Asp Thr
        195                 200                 205
Gly Leu Ser Asp Phe Val Pro Gln Asp Ile Gln Lys Leu Trp His Ser
    210                 215                 220
Met Ile Pro Met Gly Arg Asp Ala Lys Ala Thr Glu Leu Lys Gly Ala
225                 230                 235                 240
Tyr Val Tyr Phe Ala Ser Asp Ala Ser Ser Tyr Cys Thr Gly Ser Asp
                245                 250                 255
Leu Leu Ile Asp Gly Gly Tyr Cys Val Arg
            260                 265
```

<210> SEQ ID NO 12
<211> LENGTH: 1026
<212> TYPE: DNA
<213> ORGANISM: Alternaria alternata

<400> SEQUENCE: 12

```
cttcatatca catcacactt caactcaatt cccattttat ataccccaaa cttctttact     60
cttcataaac ccacataatc gccacaatgc ccatcaccgt tccccaagct accgagctca    120
aggacctctt cagccttaag ggcaaggtcg tcatcgtcac cggtgcctcc ggccccaccg    180
gtattggcac agaggctgcc cgaggatgcg ctgagtacgg tgccgacctc gccatcacct    240
acaactctcg cgccgagggt gccgagaaga acgcaaagga gatgagcgag aagtacggcg    300
tcaaggtcaa ggcctacaag tgccaggtca acgagtacgc tcagtgcgag aagctcgtcc    360
```

| | | | | |
|---|---|---|---|---|
| aggacgtcat | caaggacttc | ggcaaggtcg | atgtcttcat | cgccaacgcc ggaaagactg | 420 |
| ccgacaacgg | tatcctcgac | gctaccgttg | agcagtggaa | cgaggtcatc cagaccgact | 480 |
| tgaccggtac | cttcaactgc | gcccgtgccg | ttggtctcca | cttccgcgag cgcaagactg | 540 |
| gctctctcgt | catcacctcc | tccatgtccg | gccacattgc | caacttcccc caggagcagg | 600 |
| cctcctacaa | cgttgctaag | gctggctgca | ttcacctcgc | caagtcgctc gccaacgagt | 660 |
| ggagggactt | tgcccgtgtc | aactccatct | ccctggata | cattgacact ggtctctccg | 720 |
| acttcgttcc | ccaggacatc | cagaagctgt | ggcactccat | gatccccatg ggccgtgacg | 780 |
| ccaaggctac | tgagctcaag | ggtgcctacg | tctacttcgc | atcggatgcc tcatcctact | 840 |
| gcactggttc | cgatctcctc | atcgacggtg | gttactgcgt | caggtaaacg tgtcattccg | 900 |
| gaaggaagat | gcgagtggag | gaatataata | atggacgacg | tcttgccgga agtcttgtgt | 960 |
| ccatgtaaat | agcatcgaga | catcaataaa | gcttcgcagg | tttcacatca caaaaaaaaa | 1020 |
| aaaaaa | | | | | 1026 |

NUCLEIC ACID SEQUENCE AND PROTEIN IN ADDITION TO POLYPEPTIDES CODING FOR MANNITOL DEHYDROGENASES OR PARTS THEREOF AND THE PRODUCTION AND USE THEREOF IN DIAGNOSIS AND THERAPY

This application is a national stage of PCT/EP03/02873 filed Mar. 19, 2003. The entire contents of the above-identified application are hereby incorporated by reference.

This application claims priority to DE 10214082.0 filed Mar. 28, 2002, and DE 10233676.8 filed Jul. 24, 2002, the entirety of which are hereby incorporated by reference.

In certain people, allergic reactions are caused by a wide range of substances. Not only allergies to components of animals, such as, for example, cat hairs, but also allergies to plants and plant parts, such as the pollen of flowers, are known. However, allergies to microorganisms such as, for example, molds, are also known.

The present invention relates to the major allergen of the mold *Cladosporium herbarum*. It has been found within the scope of the present invention that, surprisingly, this major allergen is a mannitol dehydrogenase (MtDH). The present invention furthermore relates to a major allergen of *Alternaria alternata*.

BRIEF DESCRIPTION OF THE FIGURES

FIG. 1 is the amino acid (SEQ ID NO:1) derived from SEQ ID NO: 2.

FIG. 2 shows the aiignment of the derived amino acid sequence of *Cladosporium herbarum* and *Cladosporium fulvum* mannitol dehydrogenase.

FIG. 3 is the complete nucleotide and protein sequence of the *Cladosporium herbarum* MtDH.

FIG. 4 shows the amino acid sequence for *Alternaria alternata* MtDH (SEQ ID NO: 11)

FIG. 5 shows the DNA sequence for *Alternaria alternata* MtDH (SEQ ID NO: 12)

FIG. 6 shows an alignment of DNA sequences for *Cladosporium herbarum* and *Alternaria alternata*.

FIG. 7 shows an alignment of DNA sequences for *Cladosporium herbarum* and *Alternaria alternata*.

One aspect of the present invention relates to a polypeptide which has at least 10 consecutive amino acids from the amino acid sequence with the sequence ID No. 1. The amino acid sequence is shown in FIG. 1, as is the corresponding DNA sequence. The invention also relates to the polypeptides with the seq. ID No. 4, 5 and 6.

The complete sequence of a polypeptide encoding a mannitol dehydrogenase is furthermore disclosed. Seq. ID No. 7 represents the nucleic acid sequence and seq. ID No. 8 the amino acid sequence thereof. The sequences are shown in FIG. 3.

A further aspect of the present invention relates to a polypeptide which has at least 10 consecutive amino acids from the amino acid sequence with the sequence ID No. 11. The amino acid sequence is shown in FIG. 4; it constitutes a major allergen which has been isolated from *Alternaria alternata*.

The amino acid sequence of the major allergen from. *Alternaria alternata*, which is mannitol dehydrogenase, is shown in FIG. 5 in the one-letter code, together with the DNA sequence encoding it (sequence ID No. 12) and the flanking nucleotide sequences at the 5' and the 3' end.

A polypeptide according to the invention preferably has at least one epitope. An epitope is understood as meaning a region to which antibodies can bind. In principle, there are linear epitopes. In this case, the amino acids which form the epitope are arranged next to one another. However, what are known as the confirmation epitopes are more frequent. These confirmation epitopes are formed by the folding of the polypeptide. Here, amino acids which are not adjacent in the sequence can come into spatial vicinity owing to the three-dimensional folding of the polypeptide, and this surface structure is bound by an antibody.

Preferably, the epitopes are specific for one mold. In principle, antibodies against virtually all amino acid sequences can be generated with the aid of suitable techniques, for example using adjuvants. The polypeptides according to the invention, however, play an important role in diagnostics and therapy. This is why the polypeptides according to the invention preferably have specific epitopes, the epitopes being specific for one mold. Frequently, proteins or polypeptides which originate from a certain organism have similarities to a corresponding protein or polypeptide which originates from a related organism. It is therefore possible that antibodies which are directed against an epitope of a certain mold also react with a corresponding epitope of a related mold.

The more specific an epitope, the less antibodies which are directed against it will react with an epitope of a homologous polypeptide from a related organism. Thus, the polypeptides according to the invention preferably have those epitopes which are specific for a mold. The polypeptides especially preferably have those epitopes which are specific for a mold of the genus *Cladosporium*. The polypeptides very especially preferably have an epitope which is specific for *Cladosporium herbarum*. Antibodies which are directed against such an epitope do not react with other polypeptides.

It has been found within the scope of the present invention that the polypeptide with the amino acid sequence ID No. 1 encodes a mannitol dehydrogenase. The present invention also relates to parts of this amino acid sequence with at least 11 amino acids. The polypeptides according to the invention preferably have at least 20 consecutive amino acids from the sequence with the sequence ID No. 1. More preferred are those polypeptides which have at least 50 consecutive amino acids, and very especially preferred are those polypeptides which have at least 100 consecutive amino acids from the amino acid sequence with the sequence ID No. 1.

The invention also relates to a polypeptide from the N-terminus with the sequence PGQQATKHESLLDQLS (seq. ID No. 4) and to two polypeptides from the C-terminal end with the sequence LDTGLSDFVVK (seq. ID No. 5) and MGRDGLAKEL (seq. ID No. 6).

The invention also relates to a polypeptide with the sequence ID No. 8 and to parts of this polypeptide which comprise an epitope. The parts according to the invention of the sequence ID No. 8 have at least 11, preferably at least 20, more preferably at least 50 and very especially preferably at least 100 consecutive amino acids from the amino acid sequence with the sequence ID No. 8.

The present invention furthermore relates to a polypeptide with the sequence ID No. 11 and to parts of this polypeptide which comprise an epitope. Such epitopes are specific for *Alternaria*, more precisely for *Alternaria alternata*. The parts according to the invention of the sequence ID No. 11 have at least 11, preferably at least 20, more preferably at least least 50 and especially preferably at least 100 consecutive amino acids from the amino acid sequence with the sequence ID No. 11.

These polypeptides preferably have at least one epitope. For example, it is possible, with the aid of hydrophilicity/hydrophobicity examinations, to identify those parts of the polypeptide which are especially suitable for immunological reactions. This can be done for example with the aid of suitable computer programs.

As an alternative, it is also possible to prepare fragments of the sequence with the aid of what is known as the Pepscan method and to test the short fragments for relevant epitopes by reacting them with sera from allergic patients. Moreover, it must be identified whether the epitopes are epitopes which are specific for a mold, in particular for a mold from the genus *Cladosporium* and/or *Alternaria* and in particular for *Cladosporium herbarum* and/or *Alternaria alternata*. This determination is carried out using suitable serum panels.

*Cladosporium* is a fungal genus which belongs to the molds. *Cladosporium* species are very frequent and occur preferentially in bogs, in forests and in gardens since they grow readily on rotten plants or on leaves. Moreover, they are found in greenhouses and in insufficiently cleaned refrigerators. *Cladosporium* also grows on textiles, for example linen fabrics. *Cladosporium* can trigger allergic reactions such as, for example, running nose, cough, sneezing, urticaria or asthma (mold allergy).

*Alternaria* is a fungal genus which belongs to the molds. *Alternaria* species occur preferentially in bogs, in forests and in gardens since they grow readily on rotten plants or on leaves. On domestic premises, they are mainly found in flour, fruit and vegetables. However, they also grow on a variety of textiles, for example linen fabrics. *Alternaria* can trigger allergic reactions such as, for example, running nose, cough, sneezing, urticaria or asthma (mold allergy).

Owing to the disclosure of the amino and nucleic acid sequence, it is possible, with the aid of recombinant techniques, to prepare shorter fragments of the complete sequence recombinantly in bacteria, for example in *E. coli*, or in higher organisms, for example insect cells, yeasts or eukaryotic cells. It is precisely short polypeptides that can also be provided readily via the chemical route with the aid of solid-phase synthesis.

The present invention furthermore relates to a vaccine which can be employed for desensitizing patients to a mold allergy. In the desensitization, patients who suffer from an allergy are brought into contact with a small amount of an antigen, whereby it is intended that neutralizing IgE antibodies are formed. The antigens with which the patient has come into contact are bound by these neutralizing antibodies. The antigen-antibody binding of antibodies of the IgE type, which trigger allergic reactions, are thereby avoided. The polypeptides according to the invention can therefore be used for preparing a vaccine. To this end, the recombinantly produced, or else chemically produced, polypeptides can be incorporated into a suitable vaccine formulation. In addition to the polypeptides, the vaccine formulation can also comprise conventional additives and formulation auxiliaries, as well as adjuvants.

The present invention also relates to the use of a polypeptide according to the invention for a diagnostic detection of a disease. Such a disease usually takes the form of an allergy. The polypeptides are employed in a suitable diagnostic detection system. This may take the form of a radioimmunoassay (RIA), or preferably also an ELISA (enzyme-linked immunosorbent assay). The usual configuration of such a diagnostic assay is known.

Another aspect of the present invention relates to nucleotides from the nucleotide sequence with the sequence ID No. 2. The nucleotide sequence with the sequence ID No. 2 is likewise shown in FIG. 1. It is part of the gene for the *Cladosporium herbarum* mannitol dehydrogenase according to the invention.

A further aspect of the present invention relates to polynucleotides with the nucleotide sequence of the sequence ID No. 7. Parts of this nucleotide sequence are likewise the subject-matter of the invention. With the aid of this nucleotide sequence or parts thereof, a desired polypeptide can be produced recombinantly in suitable host cells.

A further aspect of the present invention relates to polynucleotides with the nucleotide sequence, sequence ID No. 12. This is a nucleotide sequence which encodes the *Alternaria alternata* mannitol dehydrogenase and nucleotide sequences which are immediately adjacent to the coding region. Parts of this nucleotide sequence are also the subject-matter of the present invention.

A polynucleotide according to the invention has at least eight consecutive nucleotides, preferably at least 12, more preferably at least 20 and most preferably at least 50 consecutive nucleotides. For some fields of application, the nucleotides must be longer, in which case the polynucleotides have at least 100 consecutive nucleotides selected from the sequence ID No. 2, ID No. 7 or sequence ID No. 12.

The polynucleotides according to the invention can be used for detecting a mannitol dehydrogenase. It is preferred to detect the presence of a gene encoding this mannitol dehydrogenase from *Cladosporium herbarum* and/or *Alternaria alternata*. These methods take the form of nucleic acid amplification methods which are known per se. A suitable example for this purpose is NASBA (nucleic acid sequence based amplification) or, more preferably, polymerase chain reaction (PCR).

Since the nucleic acid sequences encoding the *Cladosporium herbarum* and *Alternaria alternata* mannitol dehydrogenase have been disclosed, it is possible to select those nucleotide sequences for the amplification which have a very high degree of homology, or even identity. It can be expected that, when using such highly-specific primers, other mannitol dehydrogenases from related organisms are also amplified since a high degree of homology in the amino acid sequences suggests a high degree of conservation in such a gene region.

Thus, it is preferred to use such highly conserved regions for nucleic acid diagnostics in the case when the antigen is to be isolated not only from *Cladosporium* and/or *Alternaria* species, but also from other mold species.

Regions which have a low degree of homology with one another are therefore better suited for fine diagnostics, that is to say for the distinction both between *Alternaria* and *Cladosporium* species and for the fine differentiation within *Cladosporium* or *Alternaria* species. FIG. 6 shows the coding regions from *Cladosporium herbarum* and *Alternaria alternata* together. Identical nucleotide sequences are shown against a black background and identify conserved regions.

Such a method can be used for detecting the presence of the mold *Cladosporium herbarum* and/or *Alternaria alternata*. Such applications are of interest not only in medical diagnostics, but also in other fields, for example in the fields of hygiene and food testing. In this context, it must be taken into consideration that *Cladosporium herbarum* is capable of growth even at relatively low temperatures of up to approximately +6° C. and that it can therefore constitute an undesired contamination in fields of food technology. The detection even of small amounts of *Cladosporium herbarum* may play an essential role in the control of foods and their quality control.

A further aspect of the present invention is the disclosure of a method for preparing a polypeptide according to the invention. First, a gene from a mold, preferably from *Cladosporium herbarum* or *Alternaria alternata*, can be amplified with the aid of the polynucleotides according to the invention and with the aid of the polymerase chain reaction. This polynucleotide can then be incorporated into a suitable vector with which a host cell is transformed. Suitable vectors multiply in the host cell, during which process the polypeptides are expressed. The host cells may take the form of conventional host cells. Suitable for this purpose are bacterial host cells such as *Escherichia coli* or *Bacillus subtilis* or yeasts such as, for example, *Saccharomyces cerevisiae* or *Pichia pastoris*.

For the purposes of the present invention, IgE immunoblots of *Cladosporium herbarum* crude extract were assayed with sera from 62 patients. An immunoreactive protein of molecular weight 29 kD, which was recognized by 61% of the patients' sera, was identified. The patients had been preselected in a skin test or blood test (RAST) and showed a positive response to *Cladosporium herbarum* extract. No other allergen in the *Cladosporium herbarum* extract reacted with such a high percentage of patients' sera. It is therefore assumed that this protein is the major allergen of *Cladosporium herbarum*.

The immunoreactive proteins disclosed within the scope of the present invention are important allergens, not only for diagnostic purposes, but also for the therapy of allergens to molds, in particular *Cladosporium* and *Alternaria* species. If appropriate, these allergens, together with other allergens, for example Alt a 1 [Unger A. et al. (1999), Clinical testing of recombinant allergens of the mold *Alternaria alternate*, Int. Arch. Allergy Immunol. 118, 220–221] and Enolase [Simon-Nobbe B. et al. (2000), IgE binding epitopes of enolases, a class of highly conserved fungal allergens, I. Allergy Clin. Immunol. 106, 887–895] can be employed both in diagnostics and for therapeutic purposes.

The two-dimensional separation by isoelectric focusing and SDS-PAGE showed this *Cladosporium herbarum* protein as a 29 kD spot and at isoelectric point at pH=5.8.

The protein was purified to homogeneity in a conventional method (example 1). The yield amounted to 1 mg. The homogeneously purified protein was then assayed in the IgE immunoblot with a pool of six patients and was highly positive (example 2).

The protein which had been purified to homogeneity was partially sequenced by Edmanic degradation, starting at the N terminus, and internal peptide sequences were determined after degradation with CNBr.

N-terminal and internal peptide sequences were determined after digestion with trypsin by subjecting approximately 50 μg of protein, which had been obtained by excising a spot from the two-dimensional electrophoresis, to Edman degradation.

Table 1 shows a list of all peptide sequences which were identified. The single-letter code was used. The amino acids which are shown against the black background in table 1 were found in the sequence of the *Cladosporium fulvum* mannitol dehydrogenase.

TABLE 1

Peptide sequences of the *C. herbarum* NADP-dependent mannitol dehydrogenase, N-terminal sequence

| | |
|---|---|
| PGQQATKHESLLDQXSXK: | a) Starting material: crude extract separated by means of 2-dimensional SDS gel<br>b) Analytical method: Edman sequencing |
| PGQQATKHESLLDQLSLKGK: | a) Starting material: native purified protein<br>b) Analytical method: Edman sequencing |
| Peptide 1 | |
| HESLLDQLSLK: | a) Starting material: crude extract separated by means of 2-dimensional SDS gel<br>b) Analytical method: MS/MS<br>c) Note: overlaps with the N-terminal sequence |
| Peptide 2 | |
| VVVVTGASGP: | a) Starting material: crude extract separated by means of 2-dimensional SDS gel<br>b) Tryptic digest<br>c) Analytical method: sequencing |
| WVVVVTGASKR: | a) Starting material: crude extract separated by means of 2-dimensional SDS gel<br>b) Tryptic digest<br>c) Analytical method: MS/MS |
| Peptide 3 | |
| QVDSYE: | a) Starting material: crude extract separated by means of 2-dimensional SDS gel<br>b) Tryptic digest<br>c) Analytical method: sequencing |
| Peptide 4 | |
| LDTGLSDFVVK: | a) Starting material: crude extract separated by means of 2-dimensional SDS gel<br>b) Tryptic digest<br>c) Analytical method: MS/MS |
| Peptide 5 | |
| MGRDGLAKEL: | a) Starting material: native purified protein<br>b) CnBr digest<br>c) Analytical method: sequencing |

The peptide sequences were compared with all the protein sequences listed in the databases (Swissprot, GenBank and the like) by computer-aided homology search. All peptides showed homology with the family of the mannitol dehydrogenases. The mannitol dehydrogenase with which the peptides show the highest degree of sequence similarity is the *Cladosporium fulvum* mannitol dehydrogenase. A purification of *Cladosporium fulvum* mannitol dehydrogenase is described in Noeldner et al., Physiological and Molecular Plant Pathology (1994) pp. 281–289. The position of these peptides in the sequence can be seen in the alignment (Table 2).

Protein alignment of the C. fulvum NADP MtDH and C. herbarum peptide sequences

```
C.fulvum     1   MPXRIPEAXXXLELLXXXGRVVVVXXXXXKGMGIEAARGCAEMGADLAITYASRAEGGL
C.herbarum       PGXQATKHXSXXLQXSLHGKXXXVTXXXXX-------------------------------

C.fulvum    61   KNAEELSKQYGIKCKAYKCXXXKXXSVEQLVKDVIQDFGKIDAFIANAGATANSGILDGS
C.herbarum       ----------------XXXXSXX-------------------------------------

C.fulvum   121   VEDWNHVVQVDLNGTFHCAKAVGHHFKERGTGSFVITSSMSGHIANYPQEQTSYNVAKAG
C.herbarum       ------------------------------------------------------------

C.fulvum   181   CIHMARSLANEWRDFARVNSISPGYIDTGLSDXXAXDIQKLWHSMIPLGRDGLAKEIKGA
C.herbarum       -------------------------LDTGLSDXVXX----------MGRDGLAKEL---

C.fulvum   241   YVYLVSDASTYTTGADIVIDGGYTCR
C.herbarum       --------------------------
```

C.fulvum MtDH: accession number: AAK67169 (seq. ID No. 3)

Length of the coding sequence: 267 amino acids (AA)
                                801 base pairs (bp)

MW: 28.6 kD pI: 6.33

Table 2

Table 2 shows the arrangement of the polypeptides with seq. ID No. 4, 5 and 6 with reference to the homology with *C. fulvum*.

Owing to these results, the enzyme activity of the protein which had been purified to homogeneity was assayed. The experiments reveal that the highly purified major allergen of *Cladosporium herbarum* is indeed a mannitol dehydrogenase which catalyzes the following metabolic reaction: Fructose+NADPH+H$^+$⇔mannitol+NADP$^+$. Furthermore, it has been found that NADH is not active as cosubstrate and that fructose-6-phosphate is also not active as substrate. Fructose-6-phosphate has an inhibitory effect on the reaction. The method of the activity determination is described in example 3.

Then, the N-terminal peptide sequence and an internal peptide sequence of the *Cladosporium herbarum* mannitol dehydrogenase were used for designing PCR primers by means of back translation. The primer selection is compiled in table 3.

TABLE 3

| DNA sequence of the oligos derived from the peptides |
| --- |
| Oligo 1: |
| derived from the N-terminal sequence of the *C. herbarum* mannitol dehydrogenase (MtDH) (see seq. ID No. 2) oligo sequence: 5' CA(A/G) CA(A/G) GC(I/C) AC(I/C) AA(A/G) CA(C/T) GA 3' |
| Oligo 2: |
| derived from peptide 4 of the *C. herbarum* MtDH oligo sequence: 5' AC(A/G) AA(A/G) TC(A/G) CT(I/C) AG(I/C) CC(A/G) GT(A/G) TC 3' |

The primers are mixtures of synthetic oligonucleotides. (A/G) . . . means that both adenine and guanine are found in the oligonucleotides at this position. The same applies to (C/T) and (I/C), where I represents the base inosine.

These primers which are shown in table 3 were used to carry out a PCR reaction with the DNA from a *Cladosporium herbarum* cDNA library constructed by the inventors (Achatz G et al., 1995, Mol. Immunol., 32; 213–27). The result was a 636 bp band. This band was sequenced by automated DNA sequencing as described by Sanger (1977, Proc. Natl. Acad. Sci. USA, 74; 5463–7) using the PCR primers as sequencing primers. Seq. ID No. 2 was identified in this process. The protein. sequence (seq. ID No. 1) derived from this DNA sequence has 87% identity with the protein sequence of the *Cladosporium fulvum* mannitol dehydrogenase. If the substitution by chemically related amino acids (for example I-V, isoleucine-valine and the like) is also taken into consideration, this value rises to 92%. With the plausible assumption that the *Cladosporium herbarum* mannitol dehydrogenase, like the *Cladosporium fulvum* mannitol dehydrogenase, has a total length of 267 amino acid, as much as 65% of the amino acid sequence of the major allergen (mannitol dehydrogenase) from *Cladosporium herbarum* were determined by firstly peptide sequencing and secondly DNA sequencing. The total sequence of this protein which is known to date, and the alignment of this sequence with the homologous *Cladosporium fulvum* sequence, are shown in FIG. 2.

EXAMPLE 1

Protein Purification

1. Ammonium Sulfate Precipitation:

Prefractioning can be achieved by an ammonium sulfate concentration of 50%, with mannitol dehydrogenase (MtDH) remaining in the supernatant.

50 mM Tris-HCl, pH 7.5 were added to the extract. Proteases were inhibited with 1 tablet of Roche Complete per 100 ml of extract and 2 mM EDTA.

The precipitation was carried out by adding solid, ground ammonium sulfate and was carried out in two steps, first 0–30%, then 30–50%. The precipitation was equilibrated for at least 45 minutes before the extract was centrifuged at 12 000 g. The supernatant was filtered and purified further via hydrophobic interaction chromatography (HIC).

2. HIC (Phenyl-Sepharose):

The supernatant from the ammonium sulfate precipitation was brought to pH 6.5 using 3 M sodium acetate. The column (8 ml Source, 15 PHE, PHARMACIA) was equilibrated with 1.2 M ammonium sulfate, 50 mM Tris-HCl, pH 7.5, 2 mM EDTA and loaded with the sample at a flow rate of 1 ml/min. After the column had been washed with 20 ml of buffer, it was eluted with a gradient of 1.2 M ammonium sulfate to 0.6 M ammonium sulfate over 40 ml.

The mannitol dehydrogenase (MtDH) fractions were pooled and prepared for the anion exchanger. The volume is concentrated via Centricon centrifuge tubes (Millipore); buffer exchange flow 50 mM Tris-HCl, pH 7.5 with the aid of PD-10 Desalting Columns (AMERSHAM-PHARMACIA).

3. Anionic Exchanger (Q-Sepharose):

The column (8 ml Source 15 Q, PHARMACIA) was equilibrated with 15 mM Tris-HCl, pH 7.5. It was eluted with a 0–300 mM NaCl gradient over 100 ml.

EXAMPLE 2

Immune Blot of the Native Purified MtDH After Separation in the SDS Gel

Native purified MtDH was separated by molecular weight in a reducing SDS gel (Laemmli U K, Nature, 1970; 27:680–5). Subsequently, the protein was transferred onto a PVDF membrane in a Western blot (Towbin H et al., Proc. Natl. Acad. Sci USA, 1979; 76:4350–4). After free binding sites had been saturated (30 minutes in blocking buffer: 50 mM sodium phosphate pH 7.5, 0.5% Tween 20, 0.5% BSA, 0.05% NaN$_3$), the membrane was incubated with patients' serum (1:10 diluted in blocking buffer). Then, the membrane was washed (with blocking buffer, 3×10 minutes) to remove unspecifically bound antibodies. Specifically bound IgE-Ab were detected with the aid of an $^{125}$I-labeled rabbit anti-human IgE antibody. After the membrane had been exposed to an X-ray film, the result was available.

Results:

1) The native purified MtDH reacts specifically with the IgE antibodies of *C. herbarum* allergy sufferers. A prominent IgE-reactive band is revealed at 29 kD.

2) The same result, viz. a prominent IgE-reactive band at 29 kD, is obtained when a *C. herbarum* total extract is separated in the SDS gel and subsequently incubated with patients' serum in an immune blot.

EXAMPLE 3

Immune Blot of the Native Purified MtDH After 2-Dimensional Separation

Native purified MtDH was separated under denaturing conditions in an isoelectric focusing (O'Farrel P H, J. Biol. Chem., 1975; 250:4007–21) according to the net charge (isoelectric point) of the protein. Thereafter, the protein separated thus was subjected to SDS gel electrophoresis (Laemmli U K, Nature, 1970; 27:680–5), whereby a separation by molecular weight took place in addition. The protein was transferred to a PVDF membrane in a Western blot (Towbin H et al., Proc. Natl. Acad. Sci. USA, 1979; 76:4350–4). After free binding sites had been saturated (30 minutes in blocking buffer: 50 mM sodium phosphate pH 7.5, 0.5% Tween 20, 0.5% BSA, 0.05% $NaN_3$), the membrane was incubated with patients' serum (1:10 diluted in blocking buffer). Then, the membrane was washed (with blocking buffer, 3×10 minutes) to remove unspecifically bound antibodies. Specifically bound IgE-Ab were detected with the aid of an $^{125}$I-labeled rabbit anti-human IgE antibody. After the membrane had been exposed to an X-ray film, the results were available:

Results:
1) The native purified MtDH reacts specifically with the IgE antibodies of *C. herbarum* allergy sufferers. A prominent IgE-reactive spot was observed at a molecular weight of 29 kD and an isoelectric point of 5.8.
2) The same result, viz. a prominent IgE-reactive spot at a molecular weight of 29 kD and an isoelectric point of 5.8 is obtained when a *C. herbarum* total extract is separated in a two-dimensional gel and subsequently incubated with patients' serum in an immune blot. An IgE-reactive protein with a molecular weight of 29 kD and an isoelectric point of 5.6 is additionally found in the total extract. This protein could be an MtDH isoform.

EXAMPLE 4

To confirm the results according to the invention, the enzyme activity was determined with the traditionally purified protein. The absorption of NADPH was measured in a photometer at 340 nm.

Reaction mix (1 ml):
50 mM Tris-HCl, pH 7.5
0.25 mM NADPH or NADH
D-fructose or fructose-6-phosphate (0.1; 0.2; 0.4; 0.6; 0.8; 1.0; 1.2 M)
$H_2O$ to 1 ml
the reaction is started with 0.5 µl of MtDH Results:
Reaction with fructose and NADPH
No reaction with fructose-6-phosphate and NADH

EXAMPLE 5

Sequence of Mannitol Dehydrogenase (MtDH)
The complete sequence of the *Cladosporium herbarum* mannitol dehydrogenase was determined as described hereinbelow.

The peptide sequences obtained by Edman degradation of the *Cladosporium* mannitol dehydrogenase which had been purified to homogeneity were used to synthesize primer mixtures for the PCR. The PCR resulted in a band of 636 nt which was firstly sequenced and secondly used as hybridization probe for screening our cDNA library. A complete *Cladosporium herbarum* mannitol dehydrogenase (MtDH) clone was isolated and sequenced. The complete sequence is shown in FIG. 3; it has 84% identity with the published sequence of the *C. fulvum* MtDH.

Table 4 shows the sequence alignment of the two mannitol dehydrogenases of *Cladosporium herbarum* and *Cladosporium fulvum*, only the amino acids which differ being shown.

Table 4: Alignment of the amino acid sequences of the C. herbarum and C. fulvum MtDHs:

```
C.fulvum    1    -MPSRIPEASHLLDLKSIVGKVVVITGASGPKGMTIEAAFQIAEMRADLAITYASRAERG
C.herbarum  1    MPGSQATKHESLLDQLSLNGKVVVVTGASGPRGRAIERAPTQAEMGAAVAITYASRACGE C.fulvum   60    LKDAESISRQMIECDAYSLGWDKTKSMIQVKWAQREKIDAFIAHMGATANSHILDI
C.herbarum 61    EEQVKELPTTVIRAPASSQVMSRECEKISDVAIKQDLAPIAKASATADSGILDI C.fulvum  120    SVLDSNHVVQVDLSVTFICAAVGHRFSRTSFTISEHRSHAHYICRDYSDVARA
C.herbarum 121   SVLANHSQVDLQGTVNCARAVGRPFPETSIILAMSGHIANFDQRDISNVARA C.fulvum  180    GCIEMARSLAHRRMLEARVIRTSTCTIDYTGLSDPAASLIKAHSMPLAPLSHAGSLRG
C.herbarum 181   GCIHSARSLAHRWDEARVIRGSPGYIDASDRAPTTQLWHSNIPYGRDSLAKSLRG C.fulvum  240    ATVLVGASTVTIGADIVIESVG
C.herbarum 241   ASVSFASIDASTITTWADLIDSGTI
```

Amino acid sequences which are shown against the black background mean identical amino acid sequences, chemically similar amino acids are shown against a grey background, and amino acids which differ are shown against the normal background.

The *C. fulvum* sequence is represented as seq. ID No: 9, and the *C. herbarum* amino acid sequence as SEQ. ID No: 10.

Table 4 shows the regions of the polypeptide which may be suitable for the detection of or a vaccine for *Cladosporium*. They are the regions with no differences.

In the regions with pronounced differences it must be presumed that the immunological reactions differ; such regions can therefore comprise highly specific epitopes.

When determining the sequence shown in FIG. 3, it was found that minor differences occurred in the nucleotide sequence in comparison with the originally isolated part-sequences. This can be attributed to differing sequences which were present in the gene library. However, these differences do not affect the present invention in any way. The invention relates to the disclosed differing sequences, since it is assumed that they are variants of the gene.

EXAMPLE 6

Expression in *E. coli*, and Reactivity with Patients' Serum

The open reading frame of MtDH was cloned into the following expression vectors:
a) pHis-Parallel 2 Vector (XhoI/BamHI) (Ref.: P. Sheffield, S. Garrard, and Z. Derewenda (1999). Overcoming expression and purification problems of RhoGDI using a family of "parallel" expression vectors. Protein Expr Purif 15, 34.)
b) pMW172 Vector (NdeI/EcoRI) (Ref.: M. Susani, P. Jertschin, C. Dolecek, W. R. Sperr, P. Valent, C. Ebner, D. Kraft, R. Valenta, and O. Scheiner (1995). High level expression of birch pollen profiling (Bet v 2) in *Escherichia coli*: purification and characterization of the recombinant allergen. Biochem Biophys Res Commun 215, 250.)

The plasmids were subsequently transformed into *Escherichia coli* strain BL21 (DE3). For the subsequent induction, 5-ml-portions of LBamp were inoculated with 50 µl of a stationary overnight culture of the two clones and the mixtures were shaken at 37° C. until a $OD_{600}$ of 0.8 had been reached (approx. 4 hours). The protein expression was induced with 0.8 mM IPTG. After incubation for 4 hours at 37° C. in a shaker-incubator, the *E. coli* suspensions were spun down for 15 minutes at 4000 rpm. The bacterial pellets were subsequently resuspended in 1 ml of 1×PBS, and 6-µl-portions of the dissolved bacterial pellets were separated by SDS-PAGE and subsequently stained with Coomassie BBR250. This gave the following results: the *E. coli* cells which had been transformed with the expression plasmids and induced with IPTG, but not the *E. coli* cells without plasmid, reveal a pronounced protein band at the molecular weight expected in each case, viz. 30 kD and approximately 33 kD, respectively (apparent molecular weight).

An IgE immune blot was carried out with the polypeptides which had been separated with the aid of a gel. The serum of a *Cladosporium*-positive allergy sufferer was used. The bound IgE antibodies were detected with the $^{125}$-I labeled rabbit anti-human IgE antibody (RAST). The two foreign proteins which were overexpressed in *E. coli* react strongly with the IgE of the patient, but not the proteins of *E. coli* itself.

EXAMPLE 7

Determination of the Frequency of the Response to Recombinant MtDH with the Aid of 30 Sera of *Cladosporium*-Positive Allergy Sufferers The experiment described in example 6 was repeated, but 30 different *Cladosporium*-positive allergy-sufferer sera which had not been preselected were used. The control revealed a very low immune reactivity of the *E. coli* extract with the second antibody (RAST). This can probably be attributed to an artifact. As expected, other controls were negative.

Among 30 patients, 20 revealed an IgE-positive band at 30 kD which was more pronounced than the weak band in the control experiment. MtDH is thus recognized by approximately two thirds of the *Cladosporium*-positive allergy sufferers. This finding is important because this experiment demonstrates that recombinant *Cladosporium herbarum* MtDH can be employed as diagnostic and therapeutic for the majority of the patients.

EXAMPLE 8

To clone the *Alternaria alternata* mannitol dehydrogenase, a cDNA bank in Lambda-ZAP (Stratagene, La Jolla, Calif., USA). This cDNA cloned library was prepared with the aid of isolated mRNA from *Alternaria alternata*.

As described above, the cDNA library was screened with a DNA probe, with initially 24 primary clones being isolated. 5 of these clones were sequenced completely. All 5 sequences were identical in the coding region. The translation of the nucleotide sequence into an amino acid sequence and the comparison with the amino acid sequence of the *Cladosporium herbarum* mannitol dehydrogenase revealed that the reading frame was complete. The sequence had 74% identity with the sequence from *Cladosporium herbarum*.

EXAMPLE 9

The open reading frame of the clone encoding the *Alternaria alternata* mannitol dehydrogenase was then recloned in the expression vector pHIS-parallel 2 [P. Sheffield et al. (1999), Overcoming expression and purification problems of RhoGDI using a family of "parallel" expression vectors, Protein Exp. Purif. 15, 34] using the restriction cleavage sites Bam H I (N-terminally) and Xho I (C-terminally). Upon expression in *E. coli* BL21 and subsequent analysis of the gene products with the aid of SDS-PAGE gel electrophoresis and Coomassie Blue staining, a pronounced protein band appeared at a molecular weight of approximately 30. kD. This corresponds approximately to the molecular weight which would be expected theoretically.

EXAMPLE 10

The following procedure was chosen for purifying the recombinantly produced protein, which is provided with a poly-His fragment at the C terminus: the *E. coli* cells with the expression vector, which express the foreign protein, the *Alternaria alternata* mannitol dehydrogenase, were first lysed in the customary manner. It was found that the recombinantly produced protein was present in insoluble form. The inclusion bodies formed by overexpression of the foreign protein were first solubilized in a buffer with 6-molar urea and subsequently purified by affinity chromatography over a nickel chelate column. The recombinantly produced mannitol dehydrogenase was applied in 6 M urea buffer. Imidazole buffer was employed for the elution. The protein-comprising fractions were subsequently purified further by preparative SDS-PAGE gel electrophoresis and analyzed, during which process it emerged that the allergen was already purified to virtually complete homogeneity. Staining with Coomassie-BB-R only revealed one band with a molecular weight of approximately 30 kD.

EXAMPLE 11

The protein prepared in accordance with example 10 was separated by gel electrophoresis and tested in an IgE immune blot with the sera of 28 patients. All of the 28 sera originated from patients who had shown a positive response to the *Alternaria alternata* crude extract and who had been pretested both in a skin test and in an RAST. A pronounced band was visible in the immune blot in the case of 9 of the patients' sera tested. This corresponds to approximately 32% of the *Alternaria alternata*-sensitized patients.

The invention claimed is:

1. The method of making a diagnostic kit comprising placing in a container a diagnostic agent, wherein said diagnostic agent comprises SEQ ID NO: 8 or consists of a fragment of SEQ ID NO: 8, wherein said fragment consists of at least 11 consecutive amino acid residues of SEQ ID NO: 8 and wherein the diagnostic agent binds human IgE antibodies and thereby detects an allergy.

2. A kit comprising a diagnostic agent and a container, wherein said diagnostic agent comprises SEQ ID NO. 8 or consists of a fragment of SEQ ID NO: 8, wherein said fragment consists of at least 11 consecutive amino acid residues of SEQ ID NO:8, and wherein the diagnostic agent binds human IgE antibodies and thereby detects an allergy.

3. A kit comprising a diagnostic agent and a container, wherein said diagnostic agent comprises the amino acid sequence of SEQ ID No: 8 and wherein the diagnostic agent binds human IgE antibodies and thereby detects an allergy.

* * * * *